United States Patent [19]
Dumas

[11] Patent Number: 5,990,315
[45] Date of Patent: Nov. 23, 1999

[54] PROCESS FOR THE PREPARATION OF SULFENTRAZONE

[75] Inventor: Donald Joseph Dumas, Wilmington, Del.

[73] Assignee: E. I. du Pont de Nemours and Company, Wilmington, Del.

[21] Appl. No.: 09/302,673

[22] Filed: Apr. 30, 1999

Related U.S. Application Data

[60] Provisional application No. 60/087,282, May 29, 1998.
[51] Int. Cl.$^6$ .................................................. C07D 249/12
[52] U.S. Cl. ........................................................ 548/263.2
[58] Field of Search ............................................ 548/263.2

[56] References Cited

U.S. PATENT DOCUMENTS 4,818,275   4/1989   Theodoridis ................................. 71/92

*Primary Examiner*—Patricia L. Morris

[57] ABSTRACT

The present invention provides a process for the preparation of N-[2,4-dichloro-5-[4-(difluoromethyl)-4,5-dihydro-3-methyl-5-oxo-1H-1,2,4-triazol-1-yl]phenyl]methanesulfonamide (I) which comprises reacting 2-(5-amino-2,4-dichlorophenyl)-4-(difluoromethyl)-2,4-dihydro-5-methyl-3H-1,2,4-triazol-3-one (II) with methanesulfonyl chloride in the presence of a catalytic amount of a source of soluble halide.

16 Claims, No Drawings

PROCESS FOR THE PREPARATION OF SULFENTRAZONE

This application claims the priority benefit of U.S. Provisional Application 60/087,282, filed May 29, 1998.

FIELD OF INVENTION

This invention relates to an improved process for preparing N-[2,4-dichloro-5-[4-(difluoromethyl)-4,5-dihydro-3-methyl-5-oxo-1H-1,2,4-triazol-1-yl]phenyl]methanesulfonamide (sulfentrazone, I).

by treatment with sodium hydroxide in aqueous ethanol to give I. This procedure employs 2.25 molar equivalents each of methanesulfonyl chloride and triethylamine. The apparent overall yield is about 66%.

In *Synthesis and Chemistry of Agrochemicals III*, American Chemical Society; Washington D.C., (1992); pages 136 and 137, Theodoridis et al disclose that compound I can be prepared directly from aryl amine II by treatment of II with methanesulfonyl chloride and pyridine in methylene chloride at room temperature. No details regarding the relative amounts of starting materials and reagents, the reaction time, or the yield are provided.

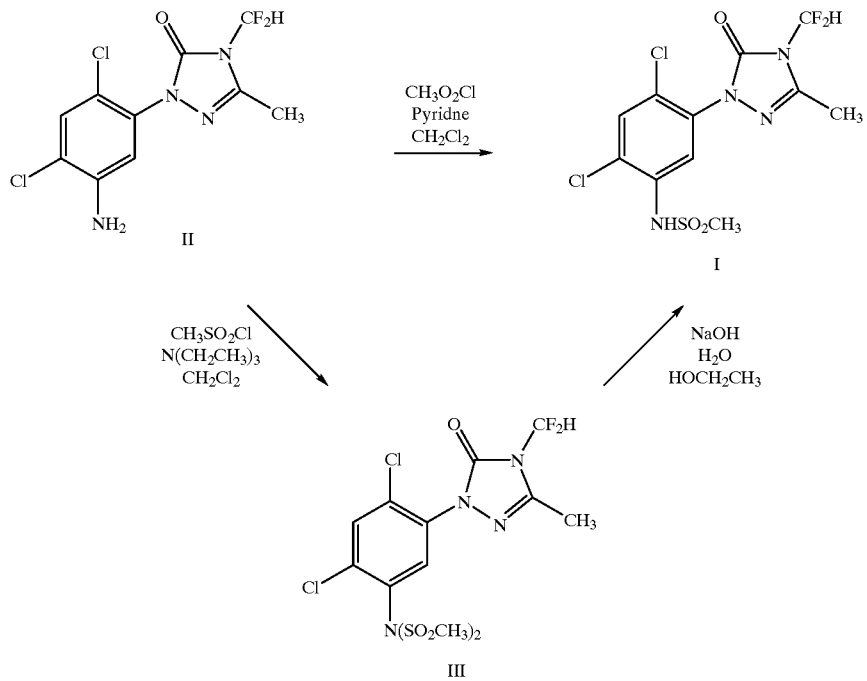

BACKGROUND OF THE INVENTION

U.S. Pat. No. 4,818,275 (Theodoridis) discloses the utility of N-[2,4-dichloro-5-[4-(difluoromethyl)-4,5-dihydro-3-methyl-5-oxo-1H-1,2,4-triazol-1-yl]phenyl]methanesulfonamide (sulfentrazone, I) as a herbicide.

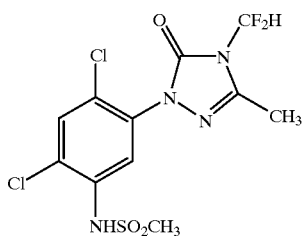

U.S. Pat. No. 4,818,275 discloses the preparation of I by treatment of the corresponding aryl amine II with methanesulfonyl chloride and triethylamine in methylene chloride, to give the bis(methanesulfonyl)amino derivative III, followed Conventional processes for the preparation of secondary methane sulfonanilides directly from primary aryl amines and methanesulfonyl chloride require the use of a molar equivalent or more, relative to the methanesulfonyl chloride, of a hydrochloric acid scavenger. This can be accomplished by using a twofold excess of the primary aryl amine or by using an amine base such as pyridine or triethylamine. In the *Journal of the American Chemical Soc.* (1929), 51, 1272–1274, Marvel et al describe the reaction of methanesulfonyl chloride with two molar equivalents of aryl amines to produce methanesulfonanilides. In the *Journal of the American Chemical Soc.* 1992, 114, 1743–1749, King et al report the preparation of methanesulfonanilide from aniline using 1 molar equivalent of methanesulfonyl chloride and 1 molar equivalent triethylamine. In *Journal of Organic Chemistry*, (1987), 52, 4377–4379, Lis and Marisca report the preparation of methanesulfonanilides using 1.1 molar equivalents each of methanesulfonyl chloride and pyridine relative to the primary aryl amine. In scaling up these processes, the hydrochloric acid scavenger must be recovered and reused or disposed of as part of the process waste streams. Recovery of the acid scavenger results in added processing costs while disposal results in increased waste treatment costs.

In the preparation of methanesulfonanilides from primary aryl amines, it is often difficult to drive the conversion of the primary aryl amine to completion without the formation of a substantial quantity of the corresponding bis(methanesulfonyl)amino derivative. In order to optimize the conversion of a primary aryl amine to a secondary sulfonamide, it is often necessary to stop the reaction when only partial conversion of the aryl amine has been achieved. This leads to reduced yields which can only be compensated for by additional processing to recover aryl amine. Alternatively, as shown by Theodoridis in U.S. Pat. No. 4,818,275, the reaction can be driven to completion and the co-product bis(methanesulfonyl)amino derivative converted back to the secondary sulfonamide. This necessitates the use of larger amounts of methanesulfonyl chloride and acid scavenger and further increases costs.

The process of the present invention avoids the problems of the prior art by providing a catalytic process which does not require the use of a molar equivalent or more of an amine base and allows for the high conversion of aryl amine II to methanesulfonamide I without the formation of substantial quantities of bis(methanesulfonyl)amino III.

SUMMARY OF THE INVENTION

This invention involves an advantageous process for preparing N-[2,4-dichloro-5-[4-(difluoromethyl)-4,5-dihydro-3-methyl-5-oxo-1H-1,2,4-triazol-1-yl]phenyl] methanesulfonamide (I) which comprising reacting 2-(5-amino-2,4-dichlorophenyl)-4-(difluoromethyl)-2,4-dihydro-5-methyl-3H-1,2,4-triazol-3-one (II) with methanesulfonyl chloride in the presence of a catalytic amount of a source of soluble halide at a temperature of from 80° to 140° C. with or without a solvent. A more preferred process is to conduct the reaction at a temperature of 100° to 120° C.

The preferred source of soluble halide for this process is generally selected from the group consisting of quaternary ammonium salts, quaternary phosphoniumn salts, salts of tertiary amines, salts of basic nitrogen containing heterocycles, salts of arylamine II, and salts of tertiary amides. A more preferred process is where the halide is chloride. A more preferred process is where a solvent is used, and a most preferred process is where this solvent is toluene.

DETAILS OF THE INVENTION

According to the present invention there is provided an improved process for the preparation of N-[2,4-dichloro-5-[4-(difluoromethyl)-4,5-dihydro-3-methyl-5-oxo-1H-1,2,4-triazol-1-yl]phenyl]methanesulfonamide (I) which comprises reacting 2-(5-amino-2,4-dichlorophenyl)-4-(difluoromethyl)-2,4-dihydro-5-methyl-3H-1,2,4-triazol-3-one (II) with methanesulfonyl chloride in the presence of a catalytic amount of a source of soluble halide.

The compound of Formula I can be prepared by the process of this invention which comprises the process variations described below.

Suitable sources of soluble halide include quaternary ammonium salts, quaternary phosphonium salts, salts of tertiary amines, salts of basic nitrogen containing heterocycles, salts of arylamine II, and salts of tertiary amides. Halide salts are preferred with chloride salts being most preferred.

Examples of useful quaternary ammonium salts include, but are not limited to, tetramethylammonium chloride, tetramethylammonium bromide, tetramethylammonium iodide, tetraethylammonium bromide, tetrapropylammonium bromide, tetrabutylammonium chloride, tetrabutylammonium bromide, tetrabutylammonium hydrogen sulfate, tricaprylymethylammonium chloride, benzyltrimethylammonium chloride, and benzyltriethylammonium chloride. Tetramethylammonium chloride is a particularly useful catalyst because of its high catalytic activity, low cost and high thermal stability.

Examples of useful quaternary phosphonium salts include, but are not limited to, tetramethylphosphonium chloride, tetramethylphosphonium bromide, tetraethylphosphonium chloride, tetraethylphosphonium bromide, tetraethylphosphonium iodide, tetrabutylphosphonium chloride, and tetrabutylphosphonium bromide.

Examples of useful salts of tertiary amines, salts of basic nitrogen containing heterocycles, and salts of arylamine II include, but are not limited to, pyridine hydrochloride, trimethylamine hydrochloride, triethylamine hydrochloride, and the hydrochloride salt of aryl amine II. Pyridine hydrochloride and the hydrochloride salt of arylamine II are particularly useful catalysts because of their high catalytic activity and thermal stability. An example of a useful tertiary amide is N,N-dimethylformamide.

In the above recitations, the term "halide" refers to fluoride, chloride, bromide, and iodide.

The solvent used in the process of this invention can be any non-reactive, aprotic solvent. The process may also be operated in the absence of a solvent. A particularly useful solvent for the process of this invention is toluene.

The process of the invention can be operated over a wide range of temperatures. Temperatures which allow for a rapid equilibration between aryl amine II and the hydrochloride salt of aryl amine II are preferred since they provide for a rapid removal of gaseous hydrochloric acid from the system. Temperatures between about 80° C. and 140° C. are preferred because they provide useful reaction rates while minimizing the decomposition of methanesulfonyl chloride. Temperatures between 100° C. and 120° C. are more preferred.

Any commercial grade of methanesulfonyl chloride can be employed in the process of this invention. While other methanesulfonating reagents, such methanesulfonyl bromide, may also be employed in the process of this invention, methanesulfonyl chloride is preferred due its substantially lower cost.

While any practical amount of methanesulfonyl chloride can be employed in the process of this invention, it is preferred that 1.3 molar equivalents or more be employed to insure a high level of conversion of aryl amine II. The amount of methanesulfonyl chloride required for high conversion of aryl amine II will depend on the specific reaction conditions and catalyst employed. The use of between 1.3 and 4.0 molar equivalents of methanesulfonyl chloride is generally sufficient.

The source of soluble halide maybe added prior to the start of the reaction or generated in situ from an appropriate precursor and the hydrochloric acid generated in the course of the reaction. When a quaternary ammonium or quaternary phosphonium salt is employed as the catalyst, it is preferred that the chloride salt be used. The halide and non-halide salts may be employed in conjunction with methanesulfonyl chloride since the hydrochloric acid generated by the reaction will convert a portion of these salts to the corresponding chlorides. When a salt of a tertiary amine, a basic nitrogen containing heterocycle, or arylamine II, or tertiary amide is employed as catalyst, the salt may be preformed or generated in situ. It is often more convenient to generate these salts in situ from the tertiary amine, basic nitrogen containing heterocycle, or arylamine II, or tertiary amide and the hydrochloric acid generated by the reaction.

The solvent, the methanesulfonyl chloride, the aryl amine II, and the catalyst or catalyst precursor can be combined at ambient temperature or after warming to the desired reaction temperature. The order in which the solvent, methanesulfonyl chloride, aryl amine II, and catalyst or catalyst precursor are combined is not critical to the success of the reaction. In practice it is often convenient to combine the solvent, aryl amine II, and catalyst or catalyst precursor and then warm the mixture to the desired reaction temperature prior to the addition of the methanesulfonyl chloride. The controlled addition of the methanesulfonyl chloride allows for a controlled evolution of hydrochloric acid gas which is vented from the reaction system.

EXAMPLE 1

Preparation of Compound I Catalyzed by Tetramethylammonium Chloride

A 250-mL, three neck round bottomed flask was equipped with a mechanical stirrer, heating mantel, thermometer, pressure equalizing addition funnel and reflux condenser. A nitrogen purge was established across the top of the condenser with all gases exiting through a caustic scrubber. The flask was charged with 53.9 g (0.143 mole, 82% assay) of 2-(5-amino-2,4-dichlorophenyl)-4-(difluoromethyl)-2,4-dihydro-5-methyl-3H-1,2,4-triazol-3-one, 1.7 g (0.015 mole) of tetramethylammonium chloride (Aldrich, 97%) and 24 g of toluene. The mixture was heated to reflux and 15.6 ml (23 g, 0.20 mole) of methanesulfonyl chloride (Aldrich, 99.5%) added dropwise over 36 minutes. Ninety minutes after the completion of the addition, a further 3.9 mL (5.75 g, 0.05 mole) of methanesulfonyl chloride was added. After an additional 1.5 hours at reflux, the reaction mixture was diluted with 75 mL of toluene, transferred to a 1-L round bottomed flask equipped with a mechanical stirrer, and rinsed in with 100 mL of toluene. The mixture was allowed to cool to room temperature and stirred overnight (15.5 hours). The resulting slurry was cooled using an ice bath for three hours, the product collected by filtration, and the filter cake washed with a total of 155 ml of cold toluene and dried in a vacuum oven to provide 57.8 g (83% yield) of 80.3% assay N-[2,4-dichloro-5-[4-(difluoromethyl)-4,5-dihydro-3-methyl-5-oxo-1H-1,2,4-triazol-1-yl]phenyl]methanesulfonamide as a tan solid.

EXAMPLE 2

Preparation of Compound I Catalyzed by in situ Generated Pyridine Hydrochloride The reaction was carried out using the same equipment as described in Example 1. The flask was charged with 53.9 g (0.143 mole, 82% assay) of 2-(5-amino-2,4-dichlorophenyl)-4-(difluoromethyl)-2,4-dihydro-5-methyl-3H-1,2,4-triazol-3-one 1.2 mL (1.17 g, 0.015 mole) of pyridine and 24 g of toluene. The mixture was heated to reflux and 15.6 mL (23 g, 0.20 mole) of methanesulfonyl chloride (Aldrich, 99.5%) was added dropwise over 25 minutes. The solution was heated at reflux for 2.5 hours after the completion of the addition and then allowed to cool to room temperature and stirred overnight (17 hours). The mixture was reheated to reflux for 30 minutes and a further 3.9 mL (5.75 g, 0.05 mole) of methanesulfonyl chloride added over 10 minutes. After an additional 2 hours at reflux, the reaction mixture was diluted with 75 mL, of toluene, transferred to a 1-L round bottomed flask equipped with a mechanical stirrer, and rinsed in with 200 mL of toluene. The mixture was warmed to 80° C. and washed twice with 150 mL portions of water with the washes being removed via pipette. The solution was allowed to cool slowly to room temperature and the resulting slurry stirred overnight (15 hours). The slurry was then cooled using an ice bath for 2.5 hours, the product collected by filtration, and the filter cake washed with a total of 130 mL of cold toluene and dried in a vacuum oven to provide 51.8 g (83% yield) of 88.9% assay 1-[2,4-dichloro-5-(N-methylsulfonylamino)phenyl]-3-methyl-4-difluoromethyl-$\Delta^2$-1,2,4-triazolin-5-one as a tan solid.

EXAMPLE 3

Preparation of Compound I Catalyzed by in situ Generated 2-(5-amino-2,4-dichlorophenyl)-4-(difluoromethyl)-2,4-dihydro-5-methyl-3H-1,2,4-triazol-3-one hydrochloride The reaction was carried out using the same equipment as described in Example 1. The flask was charged with 53.9 g (0.143 mole, 82% assay) of 2-(5-amino-2,4-dichlorophenyl)-4-(difluoromethyl)-2,4-dihydro-5-methyl-3H-1,2,4-triazol-3-one and 24 grams of toluene. The mixture was heated to reflux and 15.6 mL (23 g, 0.20 mole) of methanesulfonyl chloride (Aldrich, 99.5%) added dropwise over 22 minutes. The solution was heated at reflux for 4.5 hours after the completion of the addition, and a further 3.9 mL (5.75 g, 0.05 mole) of methanesulfonyl chloride was added over 10 minutes. After an additional 2.5 hours at reflux, the reaction mixture was diluted with 75 mL of toluene, allowed to cool to room temperature, and stirred over the weekend (62 hours). The resulting slurry was warmed to dissolve the solids, transferred to a 1-L round bottomed flask equipped with a mechanical stirrer, and rinsed in with 200 mL of toluene. The mixture was warmed to 80° C. and washed twice with 150 mL portions of water, with the washes being removed via pipette. The solution was allowed to cool slowly to 40° C. and the resulting slurry then cooled in an ice bath for 2.5 hours. The product was collected by filtration and the filter cake washed with a total of 120 mL of cold toluene and dried in a vacuum oven to provide 48.6 g (79% yield) of 90% assay of N-[2,4-dichloro-5-[4-(difluoromethyl)-4,5-dihydro-3-methyl-5-oxo-1H-1,2,4-triazol-1-yl]phenyl]methanesulfonamide as a tan solid.

What is claimed is:

1. A process for preparing N-[2,4-dichloro-5-[4-(difluoromethyl)-4,5-dihydro-3-methyl-5-oxo-1H-1,2,4-triazol-1-yl]phenyl]methanesulfonamide (1) comprising reacting 2-(5-amino-2,4-dichlorophenyl)-4-(difluoromethyl)-2,4-dihydro-5-methyl-3H-1,2,4-triazol-3-one (II) with methanesulfonyl chloride in the presence of a catalytic amount of a source of soluble halide at a temperature of from 80° to 140° C. with or without a solvent.

2. The process of claim 1 wherein the temperature is 100° to 120° C.

3. The process of claim 1 wherein the source of soluble halide is selected from the group consisting of quaternary ammonium salts, quaternary phosphonium salts, salts of tertiary amines, salts of basic nitrogen containing heterocycles and salts of arylamine II.

4. The process of claim 3 where the halide is chloride.

5. The process of claim 1 wherein a solvent is used.

6. The process of claim 5 wherein the solvent is toluene.

7. The process of claim 3 wherein a solvent is used.

8. The process of claim 7 wherein the solvent is toluene.

9. The process of claim 2 wherein a solvent is used.

10. The process of claim 9 wherein the solvent is toluene.

11. The process of claim 4 wherein a solvent is used.

12. The process of claim 11 wherein the solvent is toluene.

13. The process of claim 1 wherein the source of soluble halide is a salt of a tertiary amide.

14. The process of claim 13 where the halide is chloride.

15. The process of claim 13 wherein a solvent is used.

16. The process of claim 15 wherein the solvent is toluene.

* * * * *